US006448084B1

(12) United States Patent
Batteate et al.

(10) Patent No.: US 6,448,084 B1
(45) Date of Patent: Sep. 10, 2002

(54) MULTIPLE METAL ETCHANT SYSTEM FOR INTEGRATED CIRCUITS

(75) Inventors: Patricia M. Batteate, Santa Clara; Kristine T. Griley, San Jose, both of CA (US)

(73) Assignee: LSI Logic Corporation, Milpitas, CA (US)

( * ) Notice: Subject to any disclaimer, the term of this patent is extended or adjusted under 35 U.S.C. 154(b) by 0 days.

(21) Appl. No.: 09/487,984

(22) Filed: Jan. 20, 2000

(51) Int. Cl.$^7$ ............................................... C01N 31/00
(52) U.S. Cl. ............................ 436/5; 216/38; 216/52; 216/83; 216/84; 216/85
(58) Field of Search .......................... 216/38, 52, 83, 216/84, 85; 436/5

(56) References Cited

U.S. PATENT DOCUMENTS

| | | | | |
|---|---|---|---|---|
| 4,038,110 A | * | 7/1977 | Feng | 148/552 |
| 4,110,125 A | * | 8/1978 | Beyer | 148/363 |
| 4,383,042 A | * | 5/1983 | Coggins et al. | 436/5 |
| 5,402,807 A | * | 4/1995 | Moore et al. | 134/61 |
| 5,851,834 A | * | 12/1998 | Moo et al. | 436/5 |
| 5,890,501 A | * | 4/1999 | Kaneko et al. | 143/1.3 |
| 6,107,201 A | * | 8/2000 | Lee | 438/688 |
| 6,194,365 B1 | * | 2/2001 | Lee | 510/175 |

* cited by examiner

Primary Examiner—Jill Warden
Assistant Examiner—Yelena Gakh
(74) Attorney, Agent, or Firm—Luedeka, Neely & Graham, PC

(57) ABSTRACT

A method for preparing at least one metal layer of an integrated circuit for visual analysis. The at least one metal layer to be visually analyzed is exposed, and a solution of nitric acid, acetic acid, and ammonium fluoride is applied to the at least one metal layer. The at least one metal layer is rinsed to substantially remove the solution, and the s integrated circuit is dried. The solution is made with one part nitric acid, three parts acetic acid, and two parts ammonium fluoride. The nitric acid is a solution of about seventy percent by weight in water, the acetic acid is glacial acetic acid, and the ammonium fluoride is a solution of about forty percent by weight in water. The solution is at a temperature of about seventy degrees Fahrenheit, and is applied to the at least one metal layer by swabbing the solution onto the layer for between about ten seconds and about fifteen seconds. The step of exposing the at least one metal layer includes sawing the integrated circuit along a desired cross section. Material is further removed from the integrated circuit by abrasion until a desired cross section is exposed. The exposed at least one metal layer of the integrated circuit is polished. This method and solution is particularly useful for clarifying the physical characteristics of the metal layers, including grain size, thickness, and adhesion, which are visually analyzed with a scanning electron microscope.

14 Claims, 3 Drawing Sheets

MULTIPLE METAL ETCHANT SYSTEM FOR INTEGRATED CIRCUITS

FIELD

This invention relates to the field of integrated circuit failure analysis. More particularly the invention relates to preparing highly defined cross sectional samples of the metal layers of integrated circuits for micrographic analysis.

BACKGROUND

Micrographic analysis is an important tool in many different sectors of the microelectronics industry, including research, development, production control, and failure analysis. For example, the failure mode of certain inoperable or sub optimal integrated circuits is determined by visual inspection of the device at magnitudes on the order of 5,000 times the original size of the device, by techniques such as scanning electron microscopy.

Typically, the type of photomicrograph desired falls into one of two general categories, either a top surface analysis or a cross sectional analysis. The sample to be analyzed must typically be properly prepared in order to achieve an informative image using either one of these two techniques. Cross sectional analysis tends to present additional challenges beyond those encountered with top surface analysis. Typically, sample preparation for cross section analysis receives most of the same steps desired for sample preparation for top surface analysis, plus additional steps uniquely desired for cross sectional analysis.

For example, in order to view a device sample along a cross section, it is typically necessary to create the desired cross section in some manner. This is accomplished in a variety of ways, such as fracturing, mechanically slicing, or abrading the sample. Whichever method is used, it is desired that, except for the break along the desired cross section itself, the sectioning process does not create other physical anomalies that may confound or alter the physical characteristics of the device that is under investigation. One undesired physical anomaly that tends to occur during sectioning is blurring of the metallic layers of the integrated circuit. As these metallic layers tend to be relatively ductile as compared to the other layers, there is some tendency for one or both of two different types of blurring to occur.

First, blurring of the metal within a single layer of a thin film tends to hide the physical characteristics of the metal, such as grain size. Second, blurring between the different metal layers of a multiple metal layer thin film, which layers are typically disposed one upon the other, tends to obscure the interfaces at which a layer of one metal type ends and a layer of another metal type begins.

While certain of the known techniques for physically sectioning the integrated circuit tend to produce generally better results in this regard than others of the known sectioning techniques, control of metallic layer blurring tends to be insufficiently controlled by sectioning techniques alone. Further, even when very little blurring or no blurring at all is evident, sectioning techniques alone tend to produce cross sections where very little if any resolution of grain size or distinction between the different metal layers is detected.

What is needed, therefore, is a system to both resolve the interfaces between the layers of multiple layer metal films so that the different metal layers are more readily detectable, and also to clarify the individual metal layers of those multiple layer metal films to help resolve the physical characteristics of the individual metal layers.

SUMMARY

The above and other needs are provided by a method for preparing at least one metal layer of an integrated circuit for visual analysis. The at least one metal layer to be visually analyzed is exposed, and a solution of nitric acid, acetic acid, and ammonium fluoride is applied to the at least one metal layer. The at least one metal layer is rinsed to substantially remove the solution, and the integrated circuit is dried.

In various preferred embodiments, the solution is made with one part nitric acid, three parts acetic acid, and two parts ammonium fluoride. The nitric acid is a solution of about seventy percent by weight in water, the acetic acid is glacial acetic acid, and the ammonium fluoride is a solution of about forty percent by weight in water. The solution is preferably at a temperature of about seventy degrees Fahrenheit. In a most preferred embodiment, the solution is applied to the at least one metal layer by swabbing the solution onto the layer for between about ten seconds and about fifteen seconds.

The step of exposing the at least one metal layer preferably includes sawing the integrated circuit along a desired cross section. Material is further removed from the integrated circuit by abrasion until a desired cross section is exposed. Preferentially, the exposed at least one metal layer of the integrated circuit is polished. This method is particularly useful for clarifying the physical characteristics of the metal layers, including grain size, thickness, and adhesion. In a most preferred embodiment, the exposed and clarified metal layers are visually analyzed with a scanning electron microscope.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
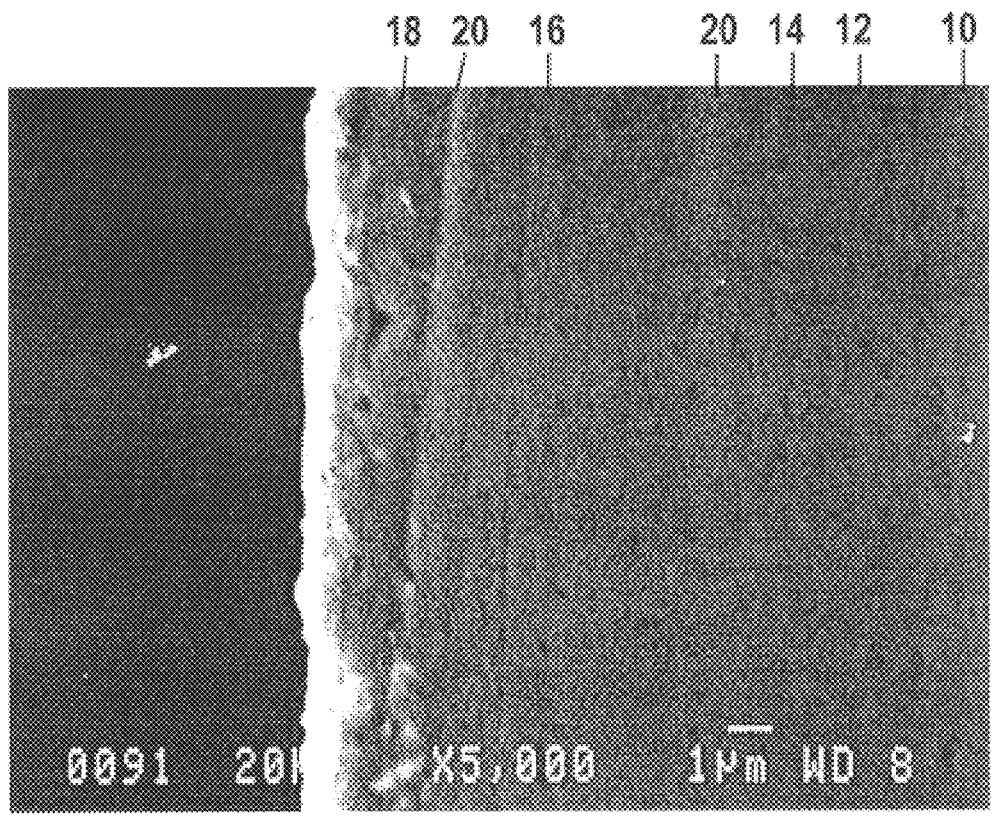
FIG. 1 is a photomicrograph of a cross section of a multiple layer metal thin film prior to applying a solution according to the invention.

With reference now to FIG. 1, there is depicted a cross section of a portion of an integrated circuit, as viewed under a scanning electron microscope. FIG. 1 particularly depicts a portion of the metal thin film layers that have been deposited on the substrate 10. In the example depicted in FIG. 1, the integrated circuit is a semiconductor device on a silicon substrate 10. However, the methods and solutions according to the present invention are not necessarily limited to silicon semiconductor devices.

The device depicted in FIG. 1 is a packaged device that experienced a failure. The purpose of visually inspecting the device is to determine, if possible, the nature and cause of the failure. If the nature of the failure relates to the physical characteristics of the metal layers on the device, then the methods of the present invention may help determine the actual cause of the failure.

The device depicted in FIG. 1 is prepared by first encapsulating, at least partially, the packaged device in an epoxy, such as that sold under the trade name Epo-Kwick, and manufactured by Buehler USA. The epoxy is allowed to cure and harden on the packaged device for about an hour. After the epoxy is sufficiently hardened, the metal layers in the approximate location of the desired cross section are exposed.

If the specific cross section desired is sufficiently deep within the package, then it may be preferred to initially cut the packaged device, such as with a saw, near but not past the location of the desired cross section. By cutting the package and the integrated circuit within it to this location, the time required to expose the desired metal layers may be reduced.

Regardless of whether or not the packaged device is cut to a location near the desired cross section, the specific location is preferably exposed by further abrading the packaged device to wear away the material of the device to the desired cross section. This is preferably done in stages, with a relatively coarser abrasive material used at the onset, and a relatively finer abrasive material used near the end of the process, as the distance between the current cross section and the desired cross section is reduced. For example, if a sanding wheel is used to abrade the packaged device, a rougher grit sand paper is used initially, and finer and finer grades are used until the metal layers at the desired cross section are exposed. At this point the desired cross section is preferably polished, such as by using a polishing pad with either a polishing slurry or a rouge.

At this point, a sample is typically rinsed and dried, then covered with a coating, such as a gold coating, to reduce electron charging in the scanning electron microscope. FIG. 1 depicts such a sample, where preparation of the metal layers has stopped at this point. As seen in FIG. 1, the interfaces 20 between the top level of gold 18, the next level of nickel 16, the next level of copper 14, and an initial level of copper 12 on the substrate 10 are all relatively faint and indistinct. Unfortunately, the polishing process described above, which removes the damage caused by creating the desired cross section, does not produce a cross section with distinct interfaces. Further, the grain structures of the different metal layers are not clarified during the sectioning and polishing processes described above.

Thus, the metal layers are preferably further prepared for visual analysis, and the metal layers clarified by further processing of the polished and cross sectioned device. This further processing is preferably accomplished by applying a solution of nitric acid, acetic acid, and ammonium fluoride to the metal layers prior to the step of gold coating the device. This solution tends to erode the softer portions of the metal layers, which tends to remove metal such as that which may have been redistributed by the sectioning and polishing process. In this manner, the interfaces between the metal layers are delineated, and the grain structure of the metal layers themselves are clarified.

The solution is preferably mixed as one part of nitric acid with three parts of acetic acid and two parts of ammonium hydroxide. The nitric acid is preferably a solution of from about 68% to about 70% by weight in water, such as that sold as catalog item number 9598-34 by J. T. Baker, a division of Mallinckrodt Baker, Inc. The acetic acid is preferably glacial acetic acid, such as that sold as catalog item number 9503-03 by J. T. Baker, a division of Mallinckrodt Baker, Inc., and the ammonium hydroxide is preferably a solution of about 40% by weight in water, such as that sold as catalog item number 109-9502 by The General Chemical Group, Inc.

The solution is preferably applied at room temperature, or in other words about seventy degrees Fahrenheit. The solution is swabbed across the cross sectional surface of the exposed metal layers for from about ten seconds to about fifteen seconds. An amount of time that is significantly less than this amount of time tends to not allow sufficient time for the solution to remove enough of the material from the metal layers to adequately clarify the physical characteristics of the metal layers. Further, an amount of time that is significantly more than this amount of time tends to give too much time for the solution to act upon the metal layers, and tends to remove too much material from the metal layers, thus tending to distort the physical characteristics of the metal layers. After swabbing, the device is rinsed liberally with filtered deionized water to remove substantially all traces of the solution, after which the device is dried. At this point the device is preferably gold coated as described above to reduce electron charging in the scanning electron microscope.

Figure 2:
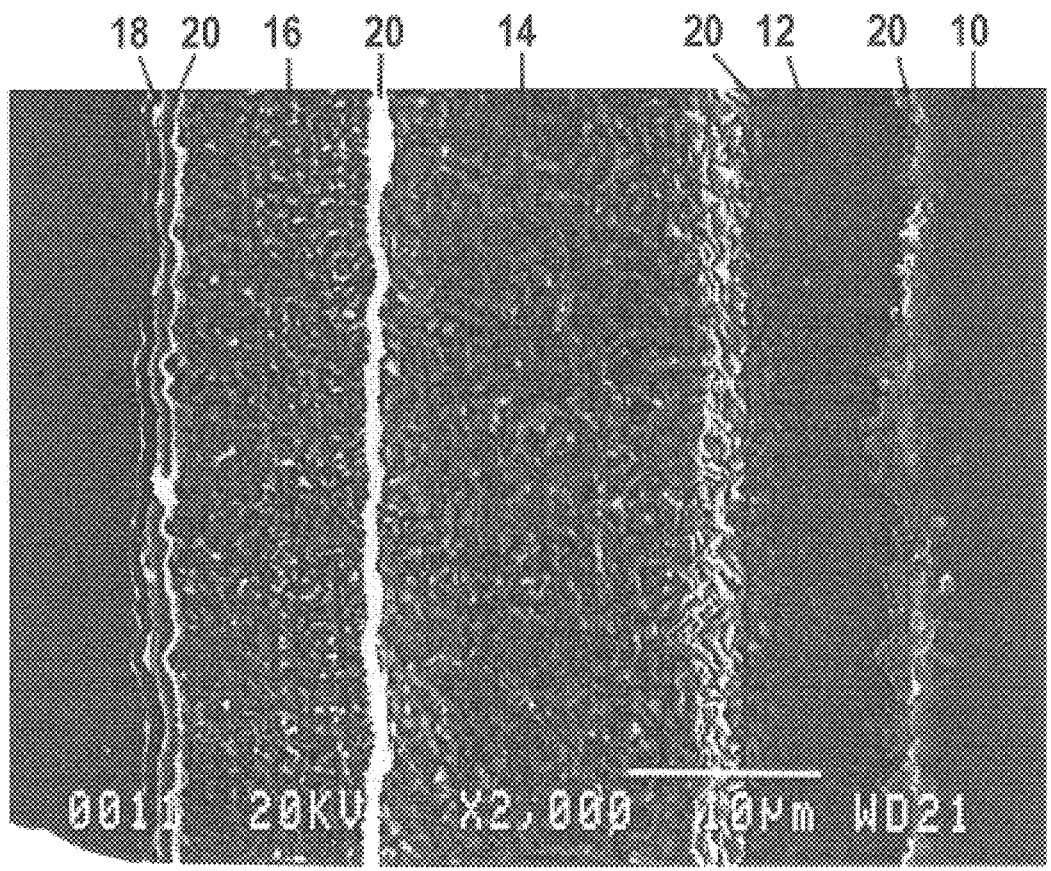
FIG. 2 is a photomicrograph of a cross section of a multiple layer metal thin film after applying a solution according to the invention.

The solution works especially well to simultaneously etch the copper layers 12 and 14, nickel layer 16, and gold layer 18 of the metal layer system depicted in FIG. 1. As depicted in the photomicrograph of FIG. 2, the metal layers after application of the solution are much more distinct than those depicted in FIG. 1. For example, the interfaces 20 between the layers are far sharper than those depicted in FIG. 1. Thus, it is more readily ascertainable whether the metal layers are contaminated or delaminating one from the other. Because it is easier to determine the interfaces 20 between the metal layers, it is also commensurately easier to determine the thickness of each of the metal layers.

Further, and as is also readily apparent, the grain structure of the individual metal layers is far more clarified in the device of FIG. 2 then in the device of FIG. 1. This degree of information in regard to the grain structure of the individual metal layers is used to determine whether the metal layers were applied using the proper processing techniques and parameters. Other information, such as contamination of the metal layers, is also determined from the grain structure.

Figure 3:
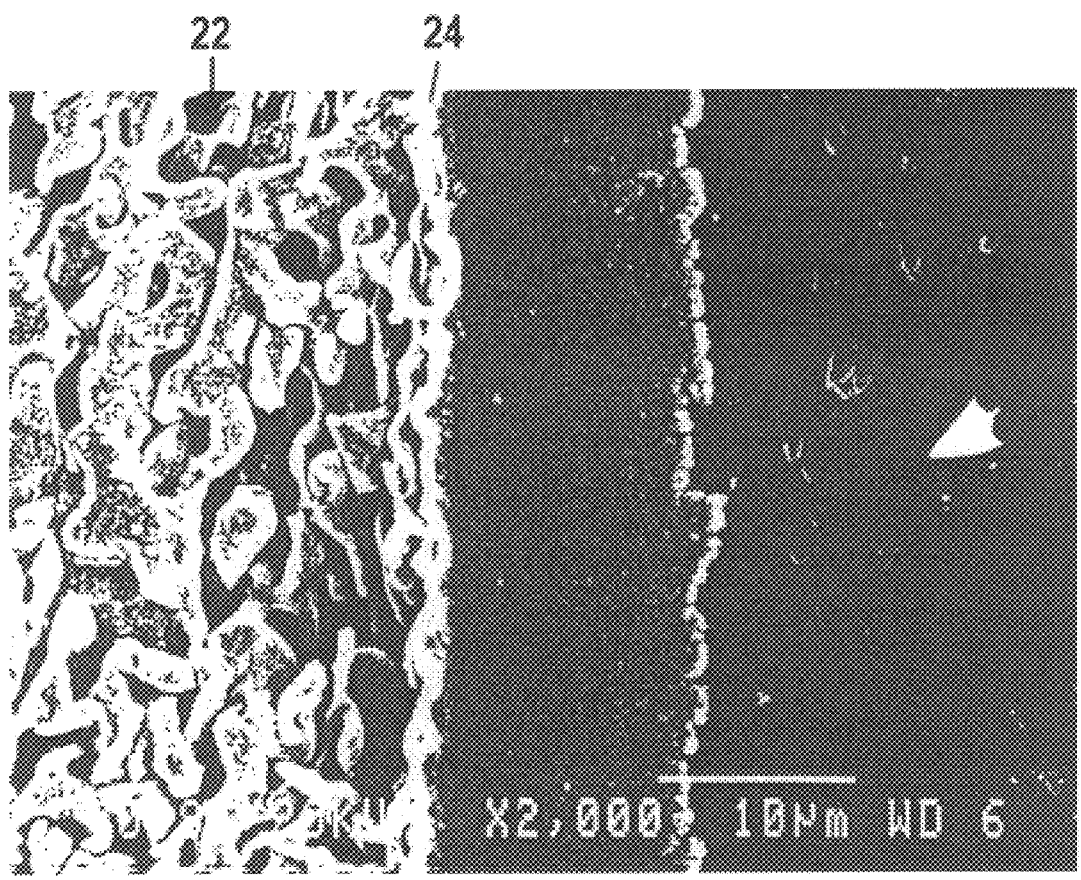
FIG. 3 is a photomicrograph of a cross section of a solder layer after applying a solution according to the invention.

Further, as seen in FIG. 3, the amount of different materials in a single metal layer is also detected. FIG. 3 depicts a cross section of a solder layer. The different regions of tin 22 and lead 24 are seen in the photomicrograph. Thus, an approximation of the relative amounts of both tin and lead in the solder layer is made with the help of this photomicrograph.

It is appreciated that the invention as described above comprehends numerous adaptations, rearrangements, and substitutions of parts, all of which are considered to be within the scope and spirit of the invention as described, and that the scope of the invention is only to be restricted by the language of the claims given below.

What is claimed is:

1. A method for preparing at least one metal layer of an integrated circuit for visual analysis, the method comprising the steps of:

exposing the at least one metal layer to be visually analyzed, applying a solution of nitric acid, acetic acid, and ammonium fluoride to the at least one metal layer, wherein the solution is applied to the at least one metal layer for between about ten seconds and about fifteen seconds, rinsing the at least one metal layer to substantially remove the solution, and drying the integrated circuit.

2. The method of claim 1 wherein the solution comprises one part nitric acid, three parts acetic acid, and two parts ammonium fluoride.

3. The method of claim 1 wherein the nitric acid comprises a solution of about seventy percent by weight in water.

4. The method of claim 1 wherein the acetic acid comprises glacial acetic acid.

5. The method of claim 1 wherein the ammonium fluoride comprises a solution of about forty percent by weight in water.

6. The method of claim 1 wherein the solution is at a temperature of about seventy degrees Fahrenheit.

7. The method of claim 1 wherein the solution is applied to the at least one metal layer by swabbing.

8. A method for preparing at least one metal layer of an integrated circuit for visual analysis, the method comprising the steps of:

exposing the at least one metal layer to be visually analyzed by sawing the integrated circuit along a desired cross section, applying a solution of nitric acid, acetic acid, and ammonium fluoride to the at least one metal layer, rinsing the at least one metal layer to substantially remove the solution, and drying the integrated circuit.

9. A method for preparing at least one metal layer of an integrated circuit for visual analysis, the method comprising the steps of:

exposing the at least one metal layer to be visually analyzed by removing material from the integrated circuit by abrasion until a desired cross section is exposed, applying a solution of nitric acid, acetic acid, and ammonium fluoride to the at least one metal layer, rinsing the at least one metal layer to substantially remove the solution, and drying the Integrated circuit.

10. A method for preparing at least one metal layer of an integrated circuit for visual analysis, the method comprising the steps of:

exposing the at least one metal layer to be visually analyzed by polishing the exposed at least one metal layer of the integrated circuit, applying a solution of nitric acid, acetic acid, and ammonium fluoride to the at least one metal layer, rinsing the at least one metal layer to substantially remove the solution, and drying the integrated circuit.

11. A method for visually analyzing physical characteristics of metal layers of an integrated circuit, the method comprising the steps of:

exposing the metal layers to be visually analyzed, applying a solution of nitric acid, acetic acid, and ammonium fluoride to the metal layers, thereby clarifying the physical characteristics of the metal layers, including grain size, thickness, and adhesion, rinsing the metal layers to substantially remove the solution, drying the integrated circuit, and visually analyzing the exposed and clarified metal layers.

12. The method of claim 11 wherein the solution further comprises one part nitric acid, three parts acetic acid, and two parts ammonium fluoride.

13. The method of claim 11 wherein the step of visually analyzing the exposed and clarified metal layers further comprises inspecting the grain sizes of the metal layers.

14. The method of claim 11 wherein the step of visually analyzing the exposed and clarified metal layers further comprises visually analyzing the exposed and clarified metal layers with a scanning electron microscope.

* * * * *